United States Patent [19]

Hasson

[11] Patent Number: 5,074,311
[45] Date of Patent: Dec. 24, 1991

[54] BIOPSY DEVICE

[76] Inventor: Harrith M. Hasson, 2043 Sedgwick, Chicago, Ill. 60614

[21] Appl. No.: 595,800

[22] Filed: Oct. 9, 1990

Related U.S. Application Data

[63] Continuation of Ser. No. 446,939, Dec. 6, 1989, abandoned.

[51] Int. Cl.⁵ .............................................. A61B 10/00
[52] U.S. Cl. .................................... 128/754; 128/755; 606/170; 606/180
[58] Field of Search .................... 128/749, 751-755; 606/167, 170, 180

[56] References Cited

U.S. PATENT DOCUMENTS

| | | | |
|---|---|---|---|
| 2,505,358 | 4/1950 | Gusberg et al. | |
| 2,516,492 | 7/1950 | Turkel. | |
| 2,729,210 | 1/1956 | Spencer. | |
| 2,749,909 | 6/1956 | Ullery et al. | |
| 3,404,677 | 10/1968 | Springer. | |
| 3,692,020 | 9/1972 | Schied. | |
| 3,989,033 | 11/1976 | Halpern et al. | |
| 3,995,619 | 12/1976 | Glatzer. | |
| 4,243,048 | 1/1981 | Griffin | 128/751 |
| 4,461,305 | 7/1984 | Cibley | 128/754 |
| 4,498,710 | 7/1986 | Kleinberg et al. | 128/751 |
| 4,651,752 | 3/1987 | Fuerst | 128/754 |
| 4,682,606 | 7/1987 | DeCaprio | 128/754 |
| 4,708,147 | 11/1987 | Haaga | 128/753 |
| 4,733,662 | 3/1988 | DeSatnick et al. | 128/751 |
| 4,785,826 | 11/1988 | Ward | 128/754 |

Primary Examiner—Randy Citrin Shay
Attorney, Agent, or Firm—Wood, Phillips, Mason, Recktenwald & Van Santen

[57] ABSTRACT

A biopsy device consisting of a housing, a coring section on the housing having a cylindrical wall with a leading cutting edge to be bored into a tissue from which a biopsy sample is to be taken and an internal hollow space bounded by an inside surface of the cylindrical wall for accepting a sample of a tissue which the cutting edge has penetrated; a severing blade with a severing edge mounted to the cylindrical wall at least partially inside of the hollow space for pivoting movement between (a) a first position wherein the severing edge is adjacent to the inside wall surface and (b) a second position wherein the severing edge is radially inwardly with respect to the cylindrical wall from the position of the severing edge in the first position, so that as the severing blade moves from the first position to the second position, the severing edge cuts across a tissue core in the internal hollow space to allow the core to be separated from the remainder of the tissue; and structure for selectively moving the severing blade between its first and second positions.

15 Claims, 3 Drawing Sheets

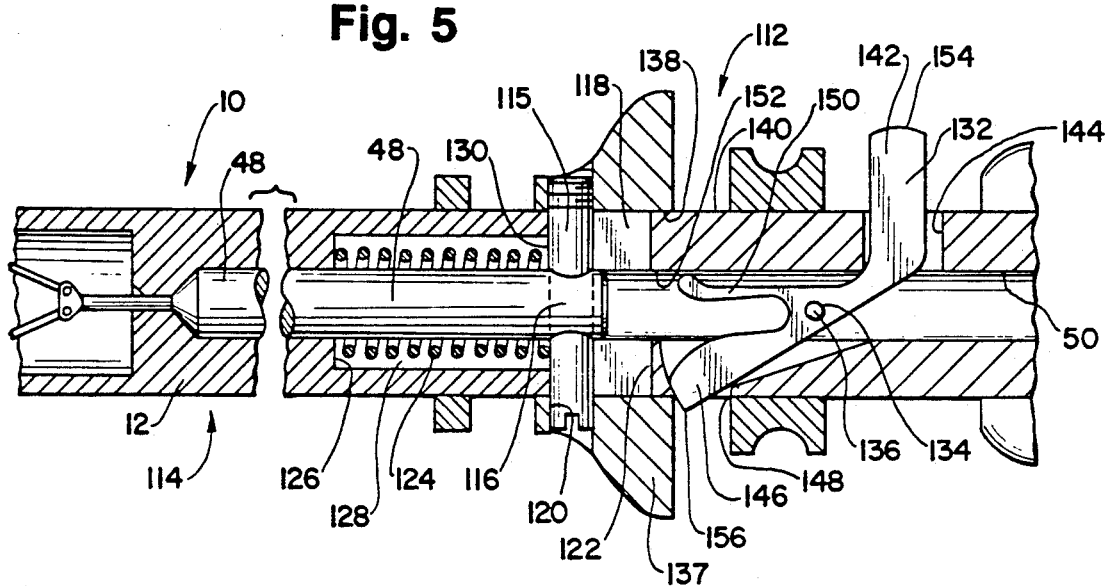
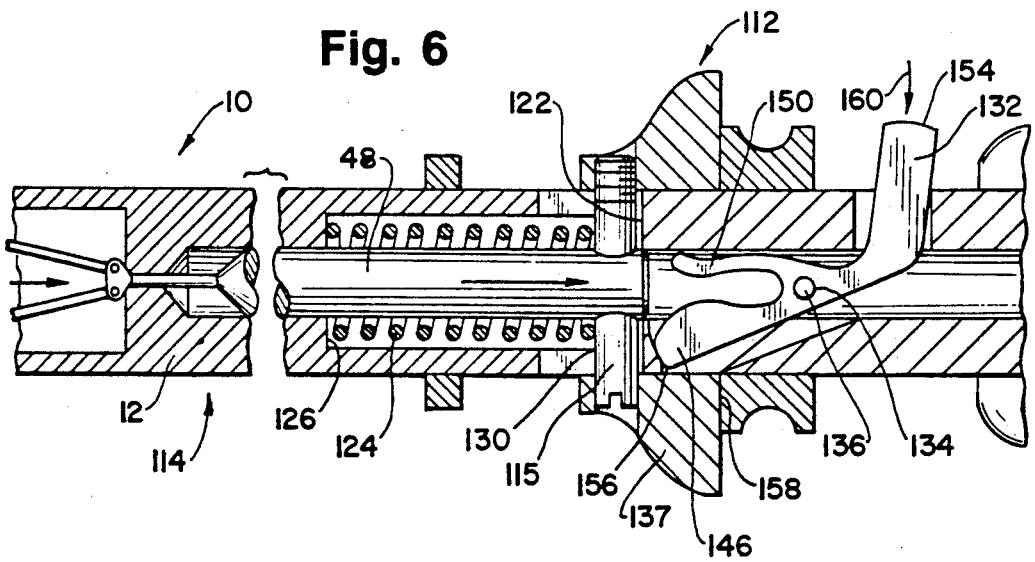

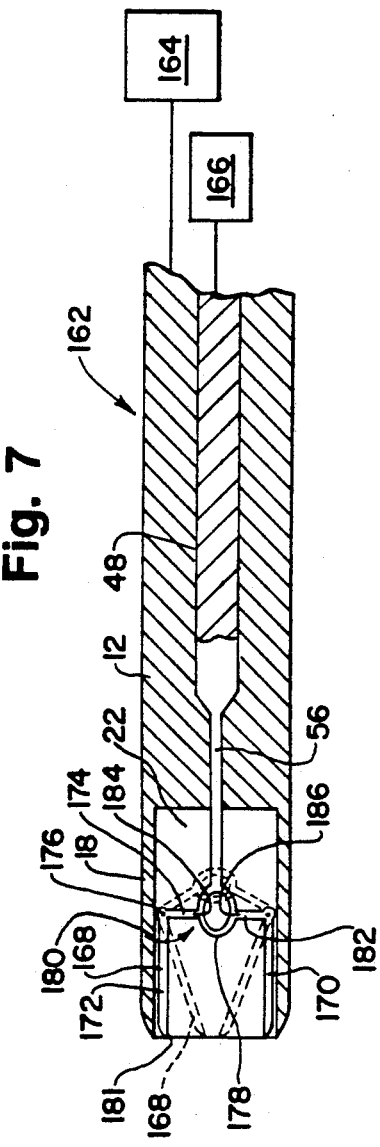
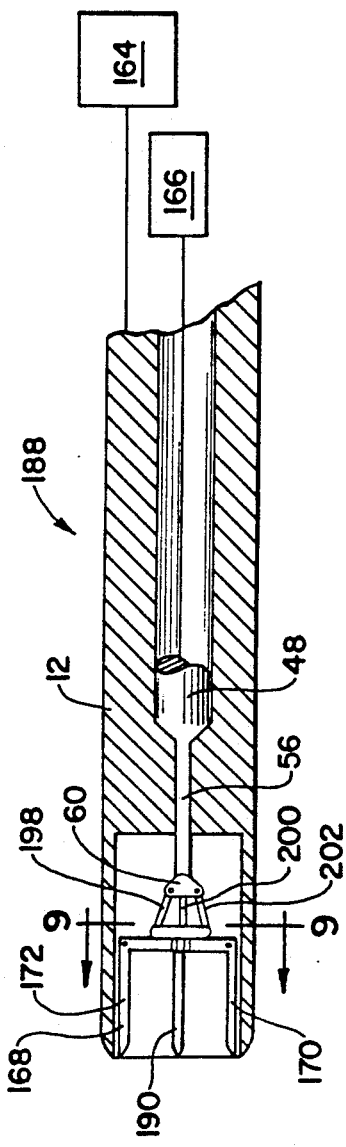
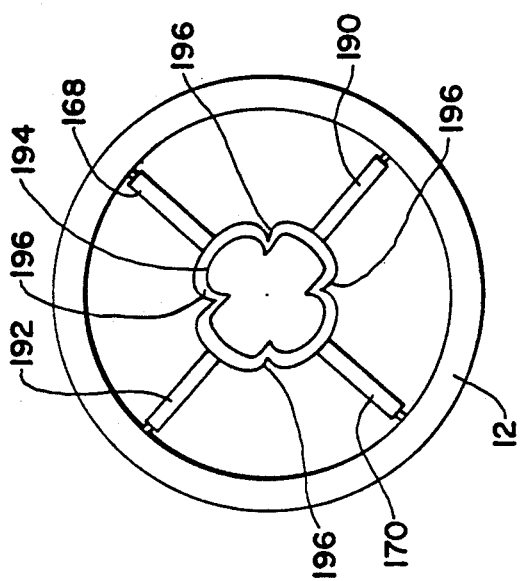

大,074,311

BIOPSY DEVICE

This application is a continuation of application Ser. No. 446,939, filed on Dec. 6, 1989, now abandoned.

BACKGROUND OF THE INVENTION

1. Field of the Invention

This invention relates to biopsy devices for excising human tissue samples and, more particularly, to such a device with which a core sample can be readily formed and severed from a tissue.

2. Background Art

Many different types of biopsy devices are known in the art. Biopsy devices are used to excise a sample of body tissue which can be conveniently analyzed by a physician.

One conventional biopsy device has an elongate configuration with a handle at one end and a coring section at the other. The coring section has a leading cutting edge which is rotated as it is pressed into the tissue from which a sample is to be taken. Rotation can be accomplished manually or by the use of a rotary device, such as a pneumatic drill, an electric drill, etc. With the cutting edge penetrating the body tissue, a core is defined which is connected at its base. Heretofore, severance of the core base has been a vexatious problem.

It is conventional to separate the core from the tissue by grasping the core with a forceps held in one hand, drawing the core outwardly with the forceps, and with a scalpel in the other hand, severing the base of the core.

While the above technique has been commonly used by physicians, it has numerous drawbacks. First, it is relatively difficult and time-consuming to perform the technique. Formation and removal of the sample core, as described above, is a four-step process.

Further, the sample may be taken from a very inconvenient location internally of the body, making the performance of the above procedure awkward, if not impossible.

A further drawback with the above technique is that severance of the core is a relatively delicate procedure which, if not performed carefully, can result in damage to the tissue surrounding the core.

SUMMARY OF THE INVENTION

The present invention is specifically directed to overcome the above enumerated problems in a novel and simple manner.

According to the present invention, a biopsy device is provided consisting of a housing, a coring section on the housing having a cylindrical wall with a leading cutting edge to be bored into a tissue from which a biopsy sample is to be taken and an internal hollow space bounded by an inside surface of the cylindrical wall for accepting a sample of a tissue which the cutting edge has penetrated; a severing blade with a severing edge mounted to the cylindrical wall at least partially inside of the hollow space for pivoting movement between (a) a first position wherein the severing edge is adjacent to the inside wall surface and (b) a second position wherein the severing edge is radially inwardly with respect to the cylindrical wall from the position of the severing edge in the first position, so that as the severing blade moves from the first position to the second position, the severing edge cuts across a tissue core in the internal hollow space to allow the core to be separated from the remainder of the tissue; and structure for selectively moving the severing blade between its first and second positions.

With the inventive structure, it is possible to bore the leading, cutting edge on the housing into the tissue and to create a core sample and, thereafter, without moving the housing, simply reposition the blade to sever the core. The core sample can be formed and separated quickly, cleanly, and with a single instrument.

The housing can be configured to readily adapt to a rotary drill, or the like, to facilitate boring of the cutting edge into tissue.

The invention contemplates different severing blade configurations, as well as the use of more than one blade to cooperatively sever the core.

In one form of the invention, the blade consists of a formed wire with a sharpened, severing edge. Preferably, the wire is formed in an L shape, with one of the legs, preferably the longer of the two legs, aligned axially of the cylindrical wall on the coring section. The blade is pivotably connected to the cylindrical wall at the juncture of the legs and the shorter leg is repositioned to move the longer leg between its first and second positions. This blade construction facilitates simple and economical manufacture of the device.

Alternatively, the blade can be made in a U-shape to nest in a recess in the cylindrical wall, with the blade in its first position. Preferably, the recess is defined by an arc centered on the pivot axis for the blade and extends radially outwardly of the inside cylindrical wall surface of its housing. The blade has a correspondingly configured portion which moves into the recess and is defined by an arc also centered on the pivot axis for the blade. In the first blade position, the blade portion moves into the recess so that there is a minimal projection into the hollow space defined by the inside surface of the cylindrical housing wall. Consequently, the nested portion of the blade will not hang up on the core sample as the coring section is bored into the tissue.

In a preferred form, there is a plurality of cooperating blades. The blades can be located in pairs at diametrically opposite portions of the cylindrical wall so that they act as jaws to sever the core sample as they are moved from their first positions into their second positions.

Bias structure is provided to urge the blade(s) into one of its first and second positions. To begin a procedure, with the blade biased into its second position, the user moves the blade against the bias into its first position. A locking structure releasably maintains the blade in its first position. Once the coring section has penetrated the tissue to a predetermined depth, the locking mechanism can be released so that under the bias force, the blade snaps from its first position into its second position, to thereby sever the core sample at its base.

In a preferred form, there is an actuating shaft which is mounted within the housing for sliding movement lengthwise thereof. The actuating shaft is connected to the blade(s) so that movement of the actuating shaft effects a desired movement of the blade(s) between the first and second positions.

With a plurality of wire-type blades employed, it is contemplated that the pivot axes therefor be at spaced locations, and preferably adjacent to the inside surface of the cylindrical wall.

BRIEF DESCRIPTION OF THE DRAWING

FIG. 5 is a section view of a biopsy device, according to the present invention, with a modified form of control structure for the severing blades and the severing blades locked in their first position against a spring bias force;

FIG. 6 is a view similar to that in FIG. 5, with the blades released under the spring bias into their second position;

FIG. 7 is a section view of a modified form of biopsy device, according to the present invention;

FIG. 8 is a section view of a still further modified form of biopsy device, according to the present invention; and FIG. 9 is a section view of the biopsy device in FIG. 8, taken along 9—9 of FIG. 8.

DETAILED DESCRIPTION OF THE DRAWINGS

Figure 1:
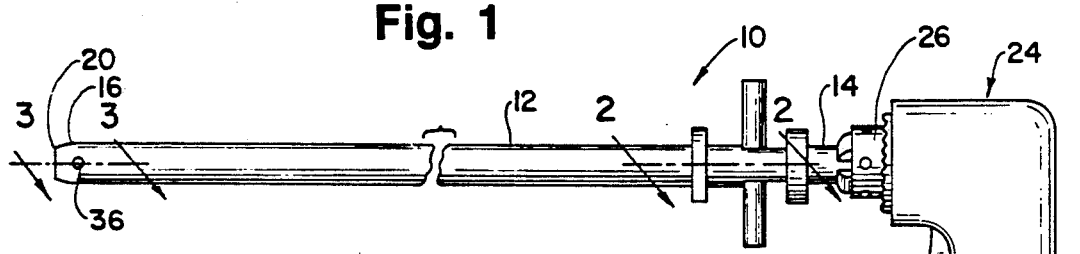
FIG. 1 is a side elevation view of a biopsy device, according to the present invention, connected to a rotary, electric drill.

One preferred form of biopsy device, according to the present invention, is shown at 10 in FIGS. 1-4. The biopsy device 10 consists of a cylindrical housing 12 having a proximal control end 14 and a distal coring end 16. The distal end 16 of the device 10 has a cylindrical wall 18, with a leading, annular, sharpened, cutting edge 20 The cylindrical wall 18 bounds a hollow space 22, dimensioned to receive a tissue core sample of a suitable size to permit analysis thereof by a physician.

In operation, the leading, cutting edge 20 of the device 10 is placed against a tissue from which a sample is to be taken. The edge 20 is pressed firmly against the tissue as the housing 12 is rotated to thereby bore the edge 20 into the tissue up to a predetermined depth. The rotation can be imparted manually or automatically, as through a rotary drill 24. The drill 24 has a chuck 26 to accept the proximal end 14 of the housing 12.

The present invention is concerned primarily with the structure shown at 28 for severing a core sample that resides within the hollow space 22 after the edge 20 is bored into a tissue. To accomplish this, first and second severing blades 30,32 are provided at diametrically opposite locations of the cylindrical wall 18. Each blade 30,32 takes a generally U shape and is pivotably attached to the wall 18 by a pin 36 for rotation about a common, radially extending axis 38. The pin 36 extends radially through and is suitably secured to, the wall 18, at diametrically opposite positions thereon.

Figure 3:
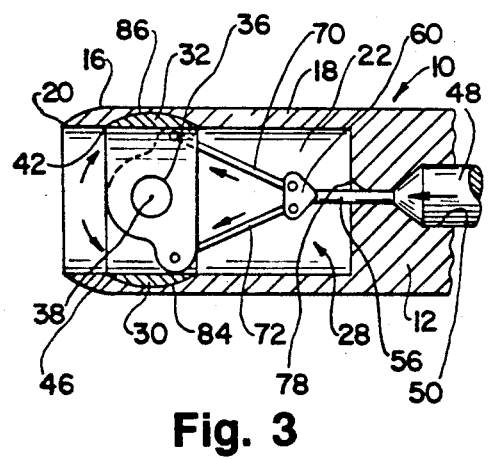
FIG. 3 is an enlarged, section view of the biopsy device, taken along line 3—3 of FIG. 1 and showing cooperating severing blades thereon in a first position.
Figure 4:
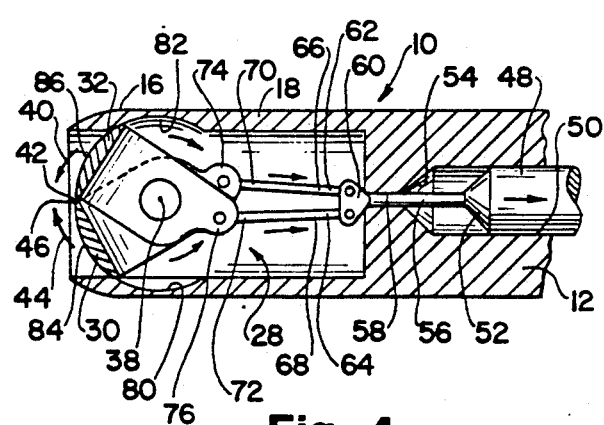
FIG. 4 is a view similar to that in FIG. 3, with the severing blades thereon in a second, severing position.

Movement of the blade 32 in the direction of arrow 40 in FIG. 4, from the FIG. 3 position, causes a severing edge 42 on the blade 32 to cut across the space 22 and thereby sever the tissue therein. Similarly, the blade 30 is pivoted in the direction of arrow 44, from the FIG. 3 position, so that the severing edge 46 cuts across the tissue in the space 22 in an opposite direction. Consequently, the blades 30,32 together act as jaws to pinch off the tissue core within the hollow space 22.

The blades 30,32 are pivoted between their FIG. 3 and FIG. 4 positions by an elongate, actuating shaft 48. The shaft 48 is received in a bore 50 through the housing 12 for sliding lengthwise movement therewithin between the FIG. 3 position and FIG. 4 position. The forward portion of the shaft 48 has a conical surface 52, which abuts a correspondingly configured seat 54 defined by the housing 12, with the shaft 48 in the FIG. 3 position, to limit forward sliding movement of the shaft 48.

The shaft 48 has a reduced diameter, forward extension 56 which extends through a bore 58 in the housing 12 so as to communicate the bore 50 with the space 22. At the free end of the extension 56, a mounting plate 60 is rigidly attached. The plate 60 pivotably connects the ends 62,64 of elongate links 66,68, respectively. The other ends 70,72 of the links 66,68 are pivotably connected to ears 74,76 on the blades 30,32, respectively.

As can be seen in FIGS. 3 and 4, with the actuating shaft 48 moved to the right, the mounting plate 60 draws the ends 70,72 towards the right, which, in turn, pivots the blade 30 in a clockwise direction about axis 38 and the blade 32 in a counterclockwise direction about axis 38, so that the severing edges 42,46 move against each other to pinch off the core sample in the space 22. The edges 42,46 abut simultaneously as the mounting plate 60 nests in a forwardly opening recess 78 in the housing 12, to prevent the edges 42,46 from being forced against each other and thereby dulled.

The above arrangement affords a very compact mounting for the blades 30,32. Diametrically opposite recesses 80,82 for the blades 30,32 are defined in the wall 18 and, at their deepest point, are traced by an arc centered on the axis 38. A matching curved outer portion 84,86 on blades 30,32 is also defined by a similar arc centered on axis 38, so that the blade portions 84,86 nest compactly in the recesses 80,82 in their FIG. 3 position so as not to obstruct the space 22 and create interference as the cutting edge 20 is bored into tissue.

Figure 2:
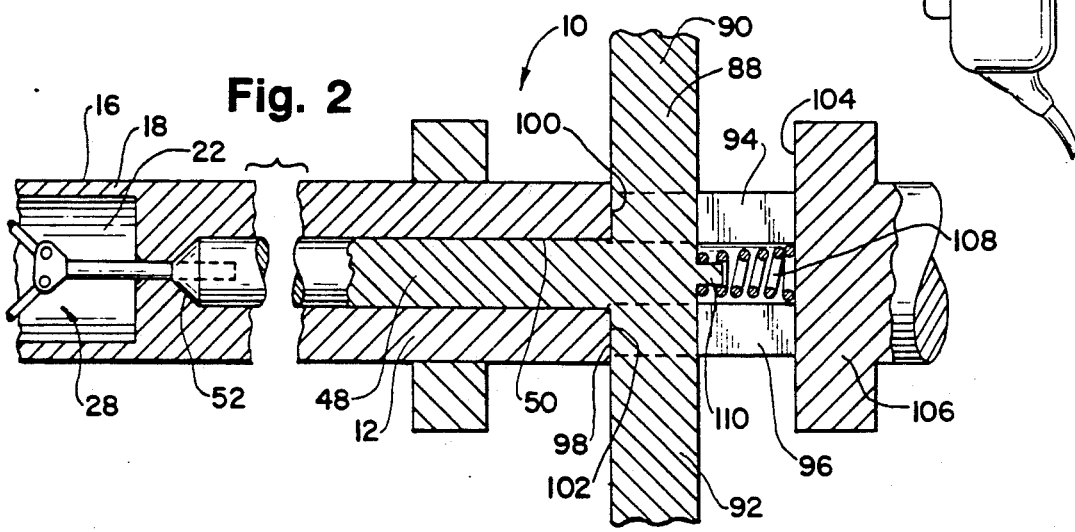
FIG. 2 is an enlarged section view of the biopsy device, taken along line 2—2 of FIG. 1.

To effect actuation of the shaft 48, an operating handle 88 is provided, as shown clearly in FIG. 2. The handle 88 has radially oppositely projecting arms 90,92, which project through elongate slots 94,96 in the housing 12. The slots 94,96 define the range of lengthwise shifting of the handle 88. In the FIG. 3 position for the blades 30,32, the forwardly facing edge 98 of the handle 88 abuts shoulders 100,102 bounding the slots 94,96, respectively. An annular, forwardly facing shoulder 104 is provided on a radially enlarged rim 106 on the housing 12, and intercepts the handle 88 to limit rearward movement to the FIG. 4 position.

A coil spring 108 surrounds a stub 110 on the handle 88 and is compressed between the handle 88 and the rim 106 so as to normally exert a bias on the handle 88 and, thus, the shaft 48, thereby urging the shaft 48 toward the solid line position in FIG. 2. Consequently, the blades 30,32 are normally biased by the spring 108 to the position shown in FIGS. 2 and 3.

After the drill 24 is operated to bore the edge 20 into the tissue, the user can manually draw the handle 88 rearwardly with two fingers, around the housing 12 and engaging the arms 90,92. The force of spring 108 must be overcome to bring the blades 30,32 into the FIG. 4 position, to thereby effect severance of the tissue core.

It should be understood that it is possible to bias the shaft 48 and associated arm 88 oppositely to the direction shown in FIG. 2. That is, the structure can be normally biased to the FIG. 4 position. In that event, the user would have to manually urge the shaft 48 forwardly to realize the FIG. 3 position before the cutting edge 20 is brought into the tissue. Once the proper cutting depth is achieved, the handle 88 can be released so that the force of spring 108 urges the structure into the FIG. 4 position. That is, the severance of the core tissue occurs automatically upon the operator releasing the handle 88.

This latter arrangement is facilitated by a locking mechanism, shown at 112 in FIGS. 5 and 6. The forward portion 114 of the device 10 is structurally the same as that shown in FIGS. 1-3. Consequently, corresponding parts are numbered the same as in FIGS. 1-3.

A pin 115 extends radially through the rear end 116 of the shaft 48. The pin 115 extends radially oppositely outwardly through the housing 12 and controls the range of movement of the shaft 48 lengthwise relative to the housing 12. Pin 115 moves in a slot 118 in the housing 12 and abuts a rearwardly facing shoulder 120 in the FIG. 5 position, corresponding to the FIG. 3 position for the blades 30,32, and abuts a forwardly facing shoulder 122, in the FIG. 6 position, which corresponds to the FIG. 4 position for the blades 30,32.

The pin 115 is normally biased to the FIG. 6 position by a coil spring 124, which surrounds the shaft 48. The spring 124 is compressed between a rearwardly facing wall 126 defined by a blind bore 128 in the housing 12, and a forwardly facing edge 130 on the pin 115.

With the mechanism in FIGS. 5 and 6, it is contemplated that the shaft 48 be preloaded and locked in the FIG. 5 position so that, upon release thereof, the spring 124 will drive the shaft 48 toward the right in FIG. 5 from the FIG. 5 position to move the blades 30,32 from the FIG. 3 position to the FIG. 4 position, to thereby sever the tissue core. Whereas the user must manually move the handle 88 in the FIG. 2 embodiment to effect severance of the tissue core, the arrangement in FIGS. 5 and 6 permits the structure to sever the core under the action of spring 124.

The shaft 48 is locked in the preloaded position of FIG. 5 by an L-shaped locking arm 132, which is mounted to the housing 12 by a pin 134 for rotation about an axis 136 between the FIG. 5 and FIG. 6 positions. The pin 115 has an associated sleeve 137, with a through bore 138 to closely surround the outer surface 140 of the housing 12 so that the sleeve 137 is slidable lengthwise thereover. The locking arm 132 has a first leg 142 projecting radially outwardly through a slot 144 in the housing 12, and a second leg 146 projecting through a separate slot 148 in the housing 12. A bias leg 150 acts against the surface 152 bounding the shaft bore 50 to normally urge the locking arm 132 into the FIG. 5 position. By depressing the free end 154 of the leg 142 radially inwardly, the bias leg 150 is deformed to allow a nose 156 on the arm 132 to move inside the slot 148 so as to reside radially within the housing surface 140, to thereby permit passage of the sleeve 137 rearwardly past the leg 146 and into the FIG. 6 position.

To preload the shaft 48, the sleeve 137 is slid to the left from the FIG. 6 position until the trailing wall 158 of the sleeve 137 moves forwardly beyond the nose 156, whereupon the residual force in the deformed bias leg 150 causes the arm 132 to pivot in a counterclockwise direction about the axis 136 into the FIG. 5 position. The leg 146 in the FIG. 5 position blocks the sleeve 137 with the blades 30,32 in the FIG. 3 position and the spring 124 loaded in compression. The tissue can then be severed by the edge 20. Once a predetermined depth is realized, the arm end 154 is radially depressed in the direction of arrow 160 sufficiently that the nose 156 moves radially inwardly to allow the sleeve 137 to move thereover. The loaded spring 124 then drives the shaft 48 into the FIG. 6 position to effect severance of a tissue core within the space 22.

A modified form of the invention is shown at 162 in FIG. 7. The device 162 has a housing 12 and a shaft 48 with an extension 56, as in the earlier described embodiments. The housing 12 is rotatable either manually or through a drill, or the like, shown schematically at 164 in FIG. 7. The shaft 48 is biased by a spring mechanism, shown schematically at 166 in FIG. 7, lengthwise of the housing 12, as in the prior embodiments. The direction of bias depends on whether a system is desired such as that in FIGS. 1-4 or that in FIGS. 5 and 6.

The principal difference between the FIG. 7 structure and those in FIGS. 1-6 is the configuration of the severing blades. In FIG. 7, two blades 168,170 are provided. Each blade 168,170 has an L shape. The blades 168,170 are located at diametrically opposite positions on the wall 18, but are otherwise the same in configuration. Consequently, the description herein will be limited to one exemplary blade 168.

The blade 168 has an L shape with a long leg 172 and a short leg 174. The blade 168 is pivoted to the housing 12 about point 176 at the juncture of the legs 172,174. The solid line position for the blade 168 corresponds to the FIG. 3 position for the blades 30,32. In this position, the long leg 172 is aligned lengthwise of the housing 12 adjacent to the inside surface 34 bounding the space 22.

The short leg 174 extends at right angles thereto. The shaft extension 56 is connected through a ring 178 to the leg 174 in such a manner that movement of the shaft 48 to the right in FIG. 7 will cause the ring 178 to draw the blade 168 in a counterclockwise direction, as indicated by arrow 180 in FIG. 7, to the phantom position. The leg 172 has a sharpened point 181 which tears through the tissue core, to effect severance thereof. In operation, the two blades 168,170 cooperate to pinch off the tissue core.

Preferably, the blades 168,170 are made from a formed piece of wire. The ring 178 is connected to the wire leg 174 on the blade 168 and the leg 182 on the blade 170, to simultaneously draw the blades 168,170 into their phantom position of FIG. 7. The ring 178 is deformable sufficiently to accommodate the variation in the effective distance between the free ends 184,186 of the legs 174,182 as the blades 168,170 pivot from their solid line to their phantom positions.

A further modified device, according to the present invention, is shown in FIGS. 8 and 9 at 188. The device 188 has a housing 12, shaft 48, and shaft extension 56, as in the FIG. 7 embodiment. Drill means 164 and bias means 166 are optionally provided, as in the FIG. 7 embodiment. There are also L-shaped blades 168,170 pivotable relative to the housing 12, as in the FIG. 7 embodiment.

The principal distinction between the structure in FIG. 8 and that in FIG. 7 is that there is an extra set of cooperating blades 190,192, in diametrically opposed relationship. The blades 190,192 operate in the same manner as the blades 168,170. Preferably, the blades 168,170, 190,192 are spaced equidistantly about the circumference of the housing 12.

A draw ring 194 connects the blades 168,170 190,192 to simultaneously pivot the blades 168,170 190,192 about their respective axes. The ring 194 has indents 196 to allow the effective diameter of the ring 194 to vary depending upon the position of the blades 168,170 190,192.

The ring 194 is connected to the mounting plate 60 on the extension 56 through four links 198,200,202 (three shown) so that sliding of the shaft 48 will effect the requisite lengthwise movement of the ring 194. In operation, the four blades 168,170, 190,192 collapse towards each other like the legs of a spider to sever the tissue core. It should be understood that any number of blades 170,172 190,192 can be used and are contemplated by the invention.

The foregoing disclosure of specific embodiments is illustrative of the board inventive concepts covered by the invention.

I claim:

1. A biopsy device comprising:

a housing:

a coring section on said housing consisting of a cylindrical wall having a leading cutting edge to be bored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement about an axis extending transverse to the axis of the cylindrical wall between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a simple tissue core in said internal hollow space to allow said tissue core to be separated from the remainder of the tissue;

means for selectively moving said severing blade between said first and second positions;

wherein said housing includes means for attaching the housing to a rotary device so that said housing and cutting edge thereon can be rotated to facilitate boring of the cutting edge into tissue.

2. A biopsy device comprising:

a housing;

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein a second severing blade is provided and mounted to the cylindrical wall in the same manner as said first claimed blade, said first claimed and second blades being moved from their first positions to their second positions to cooperatively sever a tissue core in said hollow space.

3. A biopsy device comprising:

a housing;

a coring section on said housing consisting of a cylindrical wall having a leading cutting edge to be cored into a tissue form which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein the severing blade is mounted for rotation about a first axis, a second severing blade with a severing edge is provided and is mounted to the cylindrical wall in the same manner as the first claimed severing blade for rotation about said first axis, said moving means moves the second blade between corresponding first and second positions and the moving means moves the first claimed blade and second blade in opposite directions about said first axis so that said first claimed and second blades can be moved as jaws to bring the severing edges selectively towards and away from each other.

4. A biopsy device comprising:

a housing;

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein said severing blade comprises an elongate wire with at least a portion that is substantially parallel to the axis of the cylindrical wall with the severing blade in its first position.

5. A biopsy device comprising:

a housing;

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein said severing blade comprises a wire formed in a substantially L shape with transverse legs, the wire is pivoted at the juncture of the legs and the means for moving the severing blade is connected to one of said transverse legs.

6. A biopsy device comprising:

a housing;

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein means are provided on the housing for biasing the severing blade into one of said first and second positions.

7. A biopsy device comprising:

a housing;

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein means are provided for biasing the severing blade into one of said first and second positions and means are provided for releasably holding the severing blade in the other of the first and second positions against a bias force developed by said biasing means.

8. A biopsy device comprising:

a coring section on said housing consisting of a cylindrical wall having a leading cutting edge to be cored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the cylindrical wall at least partially inside said hollow space for pivoting movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a sample tissue core in said internal hollow space to allow said tissue core to be separated from the remainder of the tissue; and means for selectively moving said severing blade between said first and second positions, wherein said housing has an elongate configuration, said means for moving the severing blade comprises an elongate actuating shaft, means are provided for mounting the housing and actuating shaft one within the other for relative lengthwise sliding movement, and the means for moving the severing blade includes means for connecting the actuating shaft to the severing blade so that movement of the actuating shaft lengthwise relative to the housing effects movement of the severing blade between its first and second positions.

9. The biopsy device according to claim 8 wherein a handle is provided externally of said housing for manually moving the actuating shaft relative to the housing.

10. A biopsy device comprising:

a housing;

a coring section on said housing consisting of a continuous cylindrical wall having a leading cutting edge to be bored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the inside surface of the cylindrical wall at least partially inside said hollow space for movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a tissue core sample in said internal hollow space to allow said core sample to be separated from the remainder of the tissue; and means movable axially relative to the cylindrical wall for selectively moving said severing blade between said first and second positions, said severing blade being movable between its first and second positions by the blade moving means without deforming the blade or the blade moving means.

11. The biopsy device according to claim 10 wherein a second severing blade is provided and mounted to the inside surface of the cylindrical wall in the same manner as said first claimed blade, said first claimed and second blades being movable to cooperatively sever a tissue core in said hollow space.

12. The biopsy device according to claim 10 wherein said cylindrical wall has a recess extending radially outwardly of said inside surface, and the severing blade resides at least partially within said recess with the severing blade in its first position.

13. A biopsy device comprising:

a housing;

a coring section on said housing consisting of a continuous cylindrical wall having a leading cutting edge to be bored into a tissue from which a biopsy is to be taken and an internal hollow space bounded by an inside surface of said cylindrical wall for accepting a sample core of a tissue which said cutting edge has penetrated;

a severing blade with a severing edge;

means for mounting the severing blade to the inside surface of the cylindrical wall at least partially inside said hollow space for movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a tissue core sample in said internal hollow space to allow said core sample to be separated from the remainder of the tissue; and means for selectively moving said severing blade between said first and second positions, wherein said cylindrical wall has a recess extending radially outwardly of said inside surface, and the severing blade resides at least partially within said recess with the severing blade in its first position, wherein the means for mounting the severing blade mounts the severing blade for pivoting movement about a first axis.

14. A biopsy device comprising:

a housing;

a coring section on said housing consisting of a continuous cylindrical wall having a leading cutting edge to be bored into a tissue from which a biopsy is to be taken and an internal hollow space bounded by an inside surface of said cylindrical wall for accepting a sample core to a tissue which said cutting edge has penetrated;

a severing blade with a severing edge;

means for mounting the severing blade to the inside surface of the cylindrical wall at least partially inside said hollow space for movement between (a) a first position wherein the severing edge is adjacent to the inside wall surface, and (b) a second position wherein the severing edge is radially inwardly with respect to said cylindrical wall from the position of said severing edge in said first position, whereby as said severing blade is moved from said first position to said second position, the severing edge cuts across a tissue core sample in said internal hollow space to allow said core sample to be separated from the remainder of the tissue; and means for selectively moving said severing blade between said first and second positions, wherein said cylindrical wall has a recess extending radially outwardly of said inside surface, and the severing blade resides at least partially within said recess with the severing blade in its first position, wherein said recess is traced by an arc centered on said first axis.

15. The biopsy device according to claim 14 wherein said severing blade has a portion defined by an arc centered on said first axis, said blade portion moving into said recess as the severing blade is moved from its second position into its first position.

* * * * *